United States Patent
Girvin et al.

(10) Patent No.: US 7,789,552 B2
(45) Date of Patent: Sep. 7, 2010

(54) PARTICULATE TESTER WITH MIXER FOR ANALYTICAL APPLICATION

(75) Inventors: Kenneth L. Girvin, Grants Pass, OR (US); Gerald A. Szpak, Grants Pass, OR (US); Keith A. Bender, Medford, OR (US); Shawn A. Hogan, Gold Hill, OR (US); Robert A. Moss, Simsbury, CT (US)

(73) Assignee: Hach Company, Loveland, CO (US)

( * ) Notice: Subject to any disclaimer, the term of this patent is extended or adjusted under 35 U.S.C. 154(b) by 1055 days.

(21) Appl. No.: 11/506,545

(22) Filed: Aug. 18, 2006

(65) Prior Publication Data

US 2007/0047385 A1    Mar. 1, 2007

Related U.S. Application Data

(60) Provisional application No. 60/709,579, filed on Aug. 18, 2005.

(51) Int. Cl.
*B01F 11/00* (2006.01)
(52) U.S. Cl. .................. 366/140; 366/142; 366/209
(58) Field of Classification Search ........... 366/142, 366/208, 209, 213, 219, 220, 232, 140
See application file for complete search history.

(56) References Cited

U.S. PATENT DOCUMENTS

RE15,677 E * 8/1923 Brown et al. ............. 366/215
2,520,556 A * 8/1950 Massey ..................... 366/209
2,539,851 A * 1/1951 Massey ..................... 366/208
3,614,434 A * 10/1971 Horwitz et al. ............ 250/364
4,061,315 A * 12/1977 Eitzen et al. .............. 366/111
4,461,578 A * 7/1984 Tiebout .................... 366/213
4,497,581 A   2/1985 Miller
5,593,228 A * 1/1997 Tannenbaum .............. 366/209
5,837,203 A   11/1998 Godec et al.
6,146,592 A   11/2000 Kawashima et al.
6,719,451 B1  4/2004 Yue
6,872,362 B2  3/2005 Schmidt et al.
6,883,958 B2  4/2005 Mayer

OTHER PUBLICATIONS

APSS-200 Automated Parenteral Sampling System (2005, Particle Measuring Systems, Boulder CO).
HIAC 9705 (2006, Hach Ultra Analytics, Grants Pass OR).
Model 9703 Liquid Particle Counting System Operations Manual (Jul. 1999, Pacific Scientific Instruments, Grants Pass OR).
Talboys Vortex Mixers (Jul. 2004, Henry Troemner LLC, Thorofare NJ.).
USP Reference Standards, General Chapter <788> Particulate Matter in Injections (2005, United States Pharmacopeia, Rockville MD).
USP Reference Standards, General Chapter <789> Particulate Matter in Opthalmic Solutions (2005, United States Pharmacopeia, Rockville MD).

* cited by examiner

*Primary Examiner*—David L Sorkin
(74) *Attorney, Agent, or Firm*—The Ollila Law Group LLC

(57) ABSTRACT

A mixer for analytical application mixes a container of fluid without a magnetic stir bar. A device for testing a liquid for particles can use the mixer. The mixing can occur in a sealed container, and liquid can be transmitted to the device from the sealed container.

18 Claims, 14 Drawing Sheets stirring mechanism exploded view

HIAC Model 9703

- 210 sample bottle
- 220 bottle mouth
- 230 mixing rod
- 240 water
- 250 polystyrene spheres
- 260 central particle void Spinning sample, looking down through sample of water magnetic stirrer velocity profile Particle diameter versus velocity necessary to overcome gravity for Polystyrene (solid, lower line) test material and for silica glass (d stirring mechanism exploded view

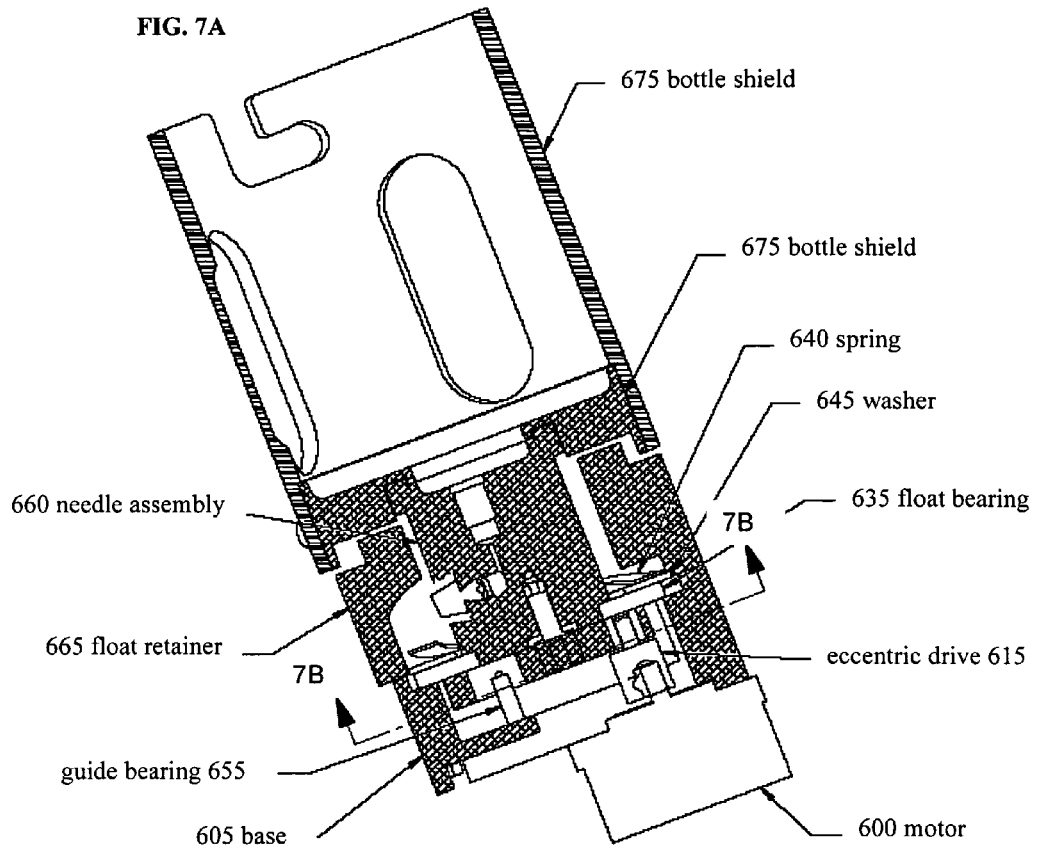
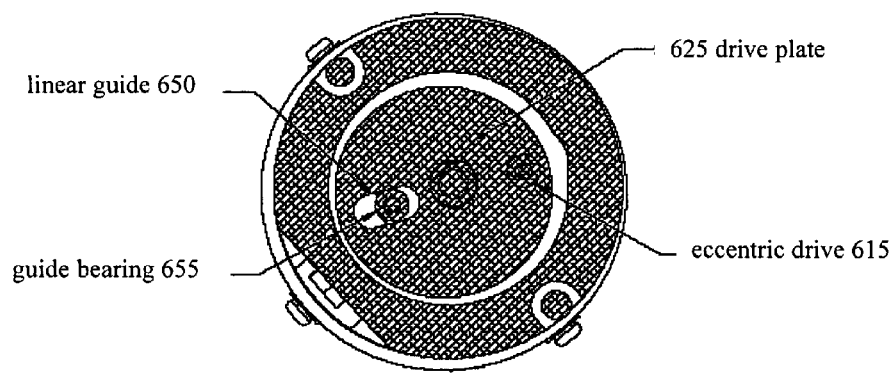

Motion Path Of Stirring Mechanism particle levels in different environments bottle being inserted fully inserted sample bottle particle counter developed wave front vortex mixed particles

PARTICULATE TESTER WITH MIXER FOR ANALYTICAL APPLICATION

RELATED APPLICATION

This application derives priority from U.S. Provisional Patent Application No. 60/709,579, filed Aug. 18, 2006.

TECHNICAL FIELD

The embodiments described in this application relate to mixing samples of liquid medical products for optical testing for particulate matter.

BACKGROUND INFORMATION

The pharmaceutical industry requires the measurement of particle size distribution for pharmaceutical production. The United States Pharmacopoeia (USP) sets mandatory limits on the size and number of particles allowed per volume of liquid. USP standards <788> Particulate Matter in Injections and <789> Particulate Matter in Ophthalmic Solutions require particulate tests and set limits for particulate content in, respectively, injections and ophthalmic solutions. The USP also sets out methods and procedures for conducting these tests.

One instrument that performs this testing is the HIAC Model 9703 Liquid Particle Counting System, shown in FIG. 1, available from Hach Ultra Analytics, Inc., of Grants Pass, Oreg., the assignee of this patent application.

A user of the Model 9703 fills a sample beaker or bottle from sample stock, degasses the sample, and then mixes the sample using (a) a magnetic stirring device built into the instrument; (b) a glass stir bar, or (c) hand agitation/swirling/mixing. The user then positions the open beaker on the instrument, and positions an intake arm into the sample within the beaker. The instrument then automatically withdraws sample fluid and tests it for particulate contamination. It uses the principle of light extinction (light blockage or obscuration) to detect particles in the range of 1.3 μm to 400 μm. The Model 9703 can use a variety of sensors in order to be able to size particles through this range. For submicron particle counting applications, the user may use the MicroCount series sensors, also from Hach Ultra Analytics.

Samples of pharmaceuticals to be tested for particulate contamination are stirred before sample testing. Samples, including blanks or known samples used for instrument validation, also should be stirred during sample testing. The USP does not dictate the exact method of stirring, although both manual and automated means are acceptable. The stirring should be such that the particle counting reproducibly sizes and counts particles in the material under investigation.

One stirring method uses a glass-stirring rod inserted into the sample, which is contained in an open beaker. Another typical stirring method inserts a magnetic stir rod, which may be Teflon coated, into the liquid sample, which is contained in an open beaker. The magnetic bar is inserted into the liquid and sinks to the bottom of the beaker. Under a plate that supports the beaker is a second magnet rotated by a motor, which turns the submerged stirring rod by magnetic coupling, thereby stirring the liquid sample. The Model 9703 comes equipped with a magnetic stirring motor. Another mixing method is to swirl the bottle by hand, without using a stirring rod.

One effect of this practice is that the material in the stirring rod itself may react with the sample under test.

Another effect is cross-contamination from transferring the magnetic or other stirring rod from one sample to another. The stir rod may be encased in a polymer "pill" to prevent metallic contamination from the rod itself, but the polymer is porous and can entrap particles or other material and transfer them from one sample to the next, despite cleaning.

Another effect is that material from the environment may become lodged on or trapped in the stirring rod. Thus, inserting the rod in the sample may transfer particles or other material from the environment to the sample to be tested.

Another effect is that the beaker or other container containing the sample is open to the atmosphere. The mixing process can increase the rate of atmospheric contamination by disturbing the liquid surface and drawing settled surface contamination into the liquid.

The stirring motion can cause other effects. A pure circular motion, like that resulting from a magnetic stirring rod, creates a symmetrical velocity profile. FIG. 2 is a still photograph of a spinning sample in a standard sample bottle 210, having a mouth 220, and containing a mixing rod 230. The photograph is taken from directly over the top of the bottle and looking down through approximately 3 inches (7.6 centimeters) of water. The bottle is filled with water 240 contaminated with 300 μm polystyrene spheres 250 and illuminated with a radial light source (not shown). The stirring rod 230, sits on the bottom of the bottle. The brightly lit area is reflection from the mouth 220 of the bottle. The current practice is to insert a sample tube into the liquid from the top of the bottle and draw the sample from the center of the liquid into the particle counter. FIG. 2 demonstrates the circular nature of this method and the particle void 260 created in the center of the liquid. This particle void 260 is created by a combination of centrifugal forces acting on the polystyrene spheres 250, of the circular liquid flow lines and of the symmetric velocity profile.

Because the bottle is stationary and the liquid is rotating, the velocity at the bottle wall is nearly zero, as is the velocity at the bottle center. FIG. 3 depicts this velocity profile 320 induced by a magnetic stirrer or spinning magnetic rod 330. The hydrodynamic drag is proportional to the square of the velocity. The velocity gradients 340 will compel particles to collect about the bottle radius/2 flow lines, where the fluid velocity is a maximum 350. Additionally, centrifugal forces (not shown) acting on the particles will compel them toward the outside of the bottle. The balance of these counteracting forces determines the radial distribution of particles around the central axis of the bottle.

This stirring motion creates a varying radial particle concentration; a sample drawn from any radial line in the liquid is probably not representative of the particle concentration of the entire sample. Current practice is to draw from the center of the bottle, which is nearly void of particles. This results in underestimating the level of sample contamination. Drawing from other parts of the sample may result in overestimating the level of sample contamination. Also, as the liquid is removed without a proportional number of particles, drawing different aliquots from the same sample may result in non-uniform measurements from aliquot to aliquot within the same sample.

Hand stirring or swirling can be non-uniform between different samples or users, and therefore may yield non-reproducible results. If the mixing is too gentle, there may be inadequate mixing in horizontal and/or vertical directions. Overly vigorous stirring may create air bubbles that may cause sample contamination or create optical artifacts. Those artifacts may be incorrectly interpreted in the testing process.

For instance, an optical testing process may incorrectly sense those bubbles as particulate contamination.

Hand stirring or swirling may be difficult or impossible to perform while a sample is being withdrawn from the beaker. The inability to mix, or to mix properly, during sample withdrawal may allow the sample to settle, so that portions of the sample that are withdrawn from the beaker may not accurately represent the concentration in the sample of materials to be tested. There may be other effects stemming from variability between users, including different elapsed times between mixing and testing.

Because the intake of the arm resides above the bottom of a flat-bottomed sample container, all the liquid below that level cannot be used for testing, and is wasted. This can be a disadvantage when testing expensive pharmaceuticals or other liquids.

SUMMARY OF THE DISCLOSURE

Preferred embodiments of a method and apparatus can be used in connection with particulate or other analytic tests.

In one aspect, the embodiments implement a method for stirring a liquid. Stirring required for analytical measurement can be accomplished during the measurement process without introducing an extra stirring device.

In another aspect, the embodiments perform stirring a sample in a sealed container. Samples can be sealed immediately after, or as part of, extraction from the production process.

In another aspects, the embodiments use a motion that creates a complex combination of vorticity and linear agitation.

Additional aspects and advantages will be apparent from the following detailed description of preferred embodiments, which proceeds with reference to the accompanying drawings.

BRIEF DESCRIPTION OF THE DRAWINGS

FIG. 7A is a cross-sectional view of the embodiment of the stirring mechanism (when assembled) of FIG. 6, and FIG. 7B is a sectional view taken along lines 7B-7B of FIG. 7A.

DETAILED DESCRIPTION OF PREFERRED EMBODIMENTS

Figure 1:
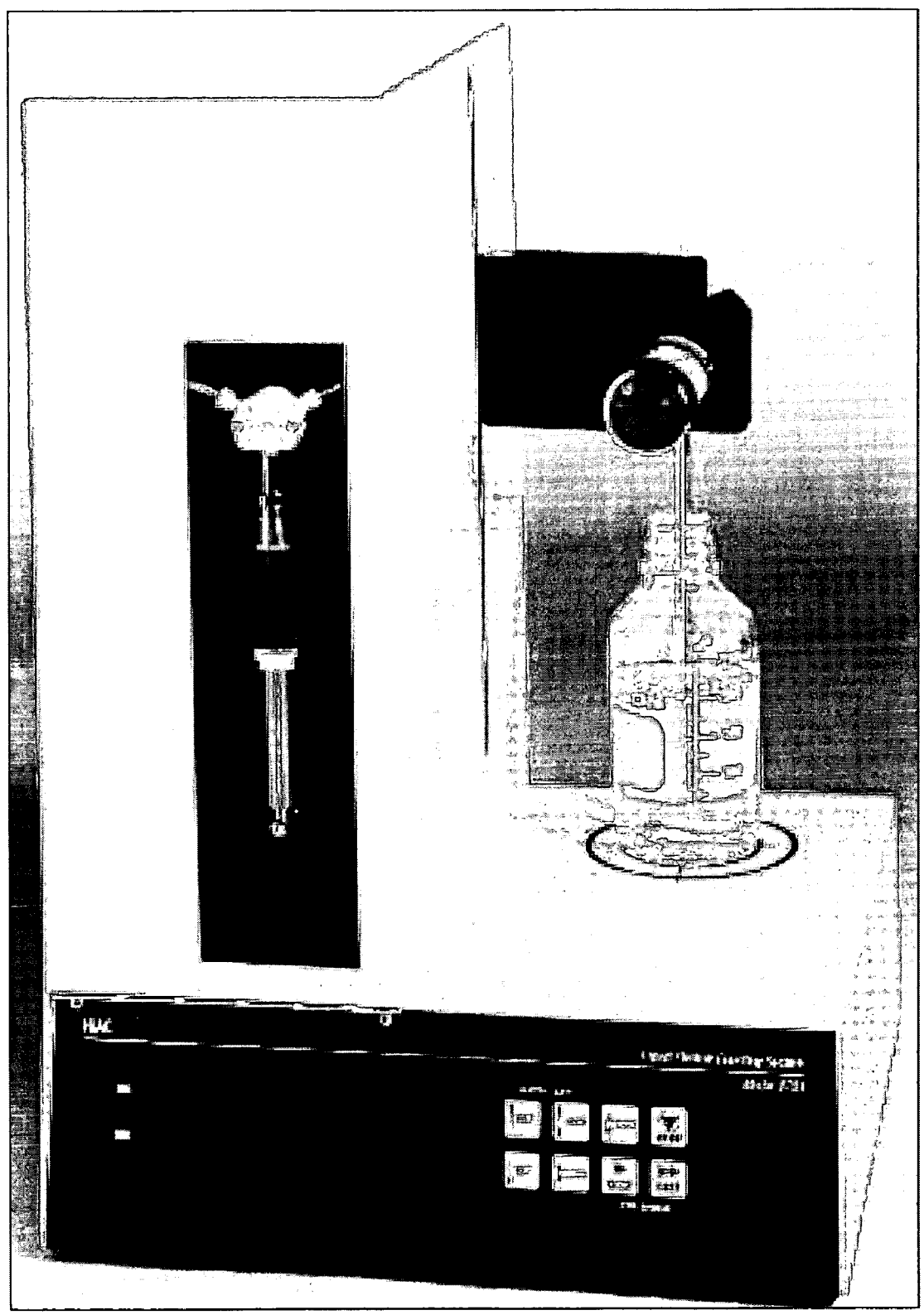
FIG. 1 is a photograph of a HIAC Model 9703 Liquid Particle Counting System.
Figure 2:
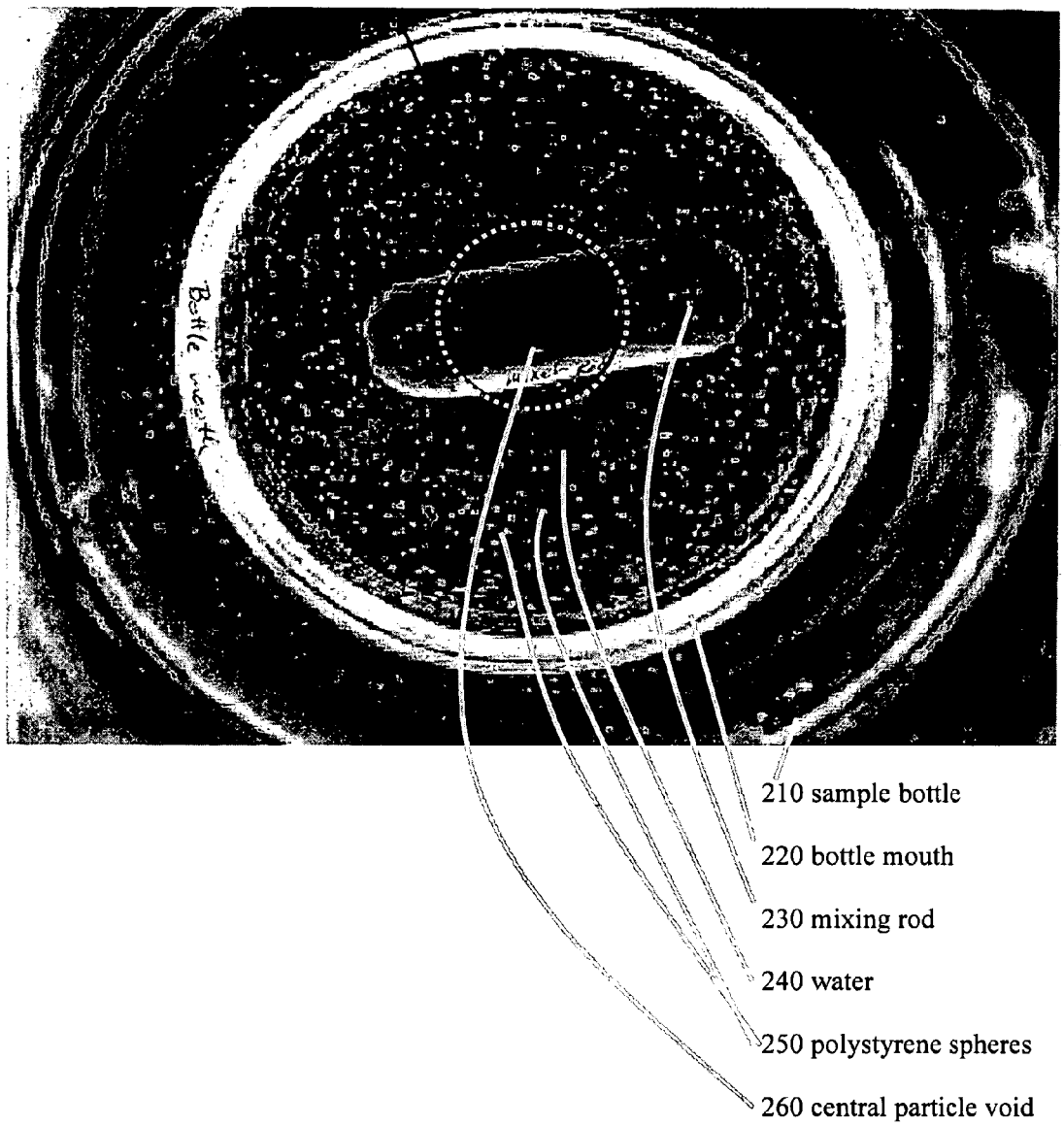
FIG. 2 is a still photograph of a spinning sample in a standard sample bottle filled with water, contaminated with 300 μm polystyrene spheres and illuminated with a radial light source.
Figure 3:
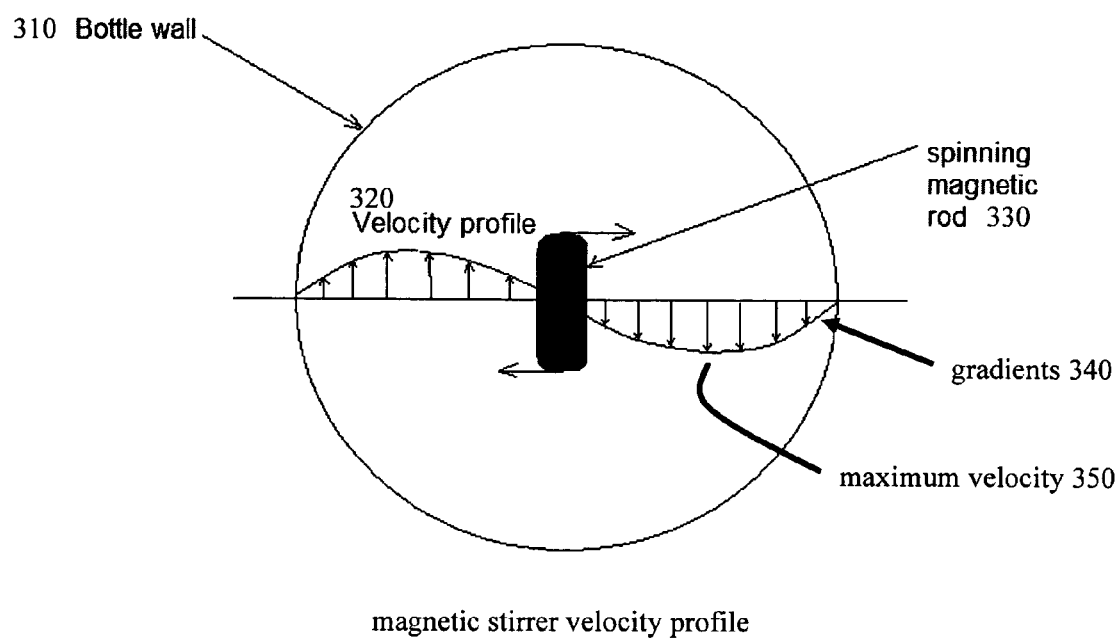
FIG. 3 depicts a magnetic stirrer velocity profile.
Figure 4:
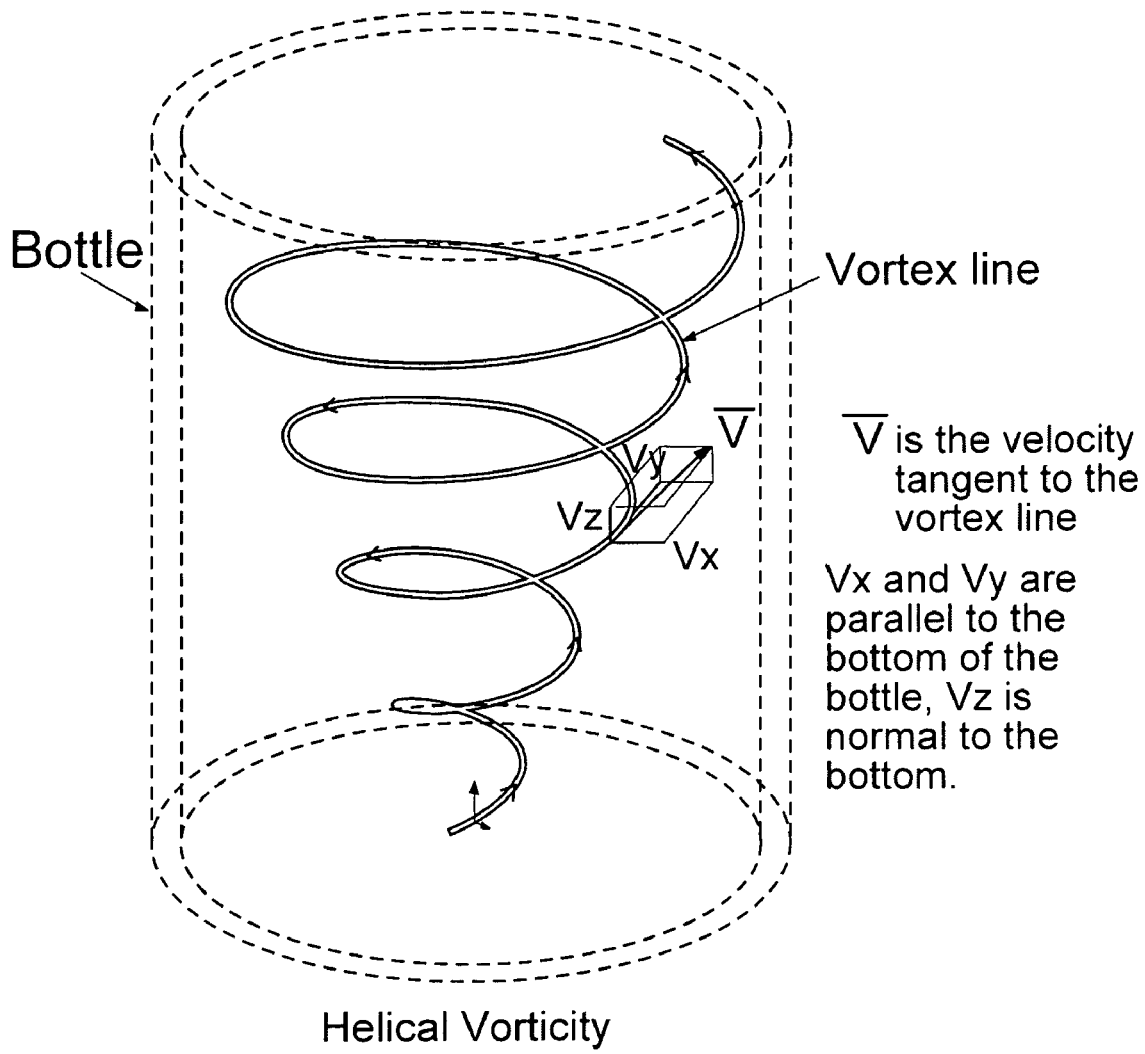
FIG. 4 is a diagram showing helical vorticity.

In one aspect, a method and mechanism induce uniform mixing into a bottle of liquid containing particle contamination. The method and mechanism can be described by starting with a simple circular motion of a bottle to generate a vortex. The circular translational motion (not rotation) of the bottle imparts momentum on a liquid mass. When the circular velocity is sufficient to overcome the ability of the liquid to adapt to the changes in direction via gravitational, centrifugal, and shear forces, the liquid will move as one mass in harmonic motion rotating about the central axis of the bottle. Centrifugal force will cause some of the liquid mass to accumulate toward one side of the bottle such that the center of mass of this liquid is offset from the central axis of the bottle, with the offset near zero at the bottom of the bottle and maximum at the surface of the liquid. This rotating mass and the gradient velocities within the liquid associated with this offset generate a vertical helical vortex as depicted in FIG. 4.

The common experience of the helical vortex is a whirlpool in a draining sink. Here the vortex lines are clearly spiraling downward through the drain. In a closed bottle the helical vortex lines spiral upward from the bottom surface of the bottle as in FIG. 4. It is a law of fluid dynamics that vortex lines must either (a) begin and end on some solid surface or (b) form closed loops. The vortex lines in the bottle begin at the bottom of the bottle and end at the bottle wall at the liquid surface. FIG. 4 also depicts the tangential velocity vector from the selected vortex line and breaks this vector into its Cartesian components: Vx, Vy, and Vz. A concern of mixing is the vertical velocity component, Vz, normal to the bottom of the bottle. This velocity component (Vz) must have a minimum magnitude to generate enough hydrodynamic drag force to overcome the gravitational force holding particles to the bottom of the bottle.

Figure 5:
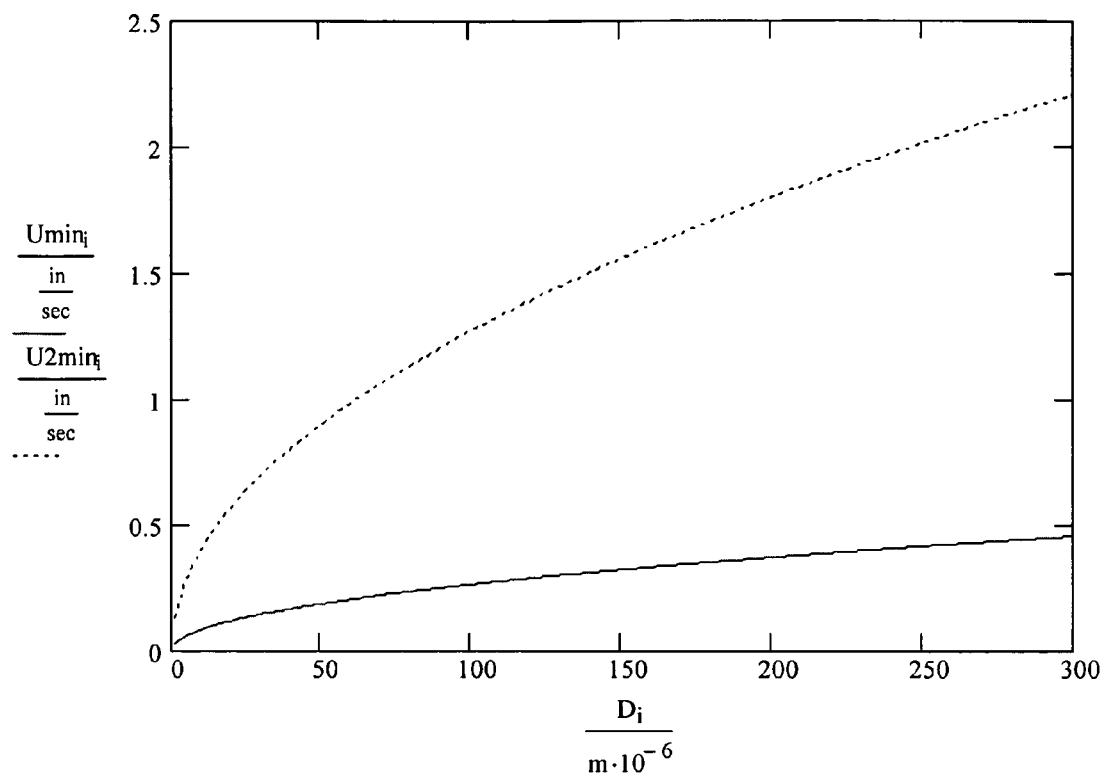
FIG. 5 is a graph of the vertical velocity component required to overcome gravitational forces for (a) polystyrene and (b) glass.

FIG. 5 shows a graph of the calculated required vertical velocity (Vz) component required to overcome gravitational forces. The graph was generated from the equation $$D_{ps} = D_2 * (\rho_2 - \rho_L)/(\rho_{ps} - \rho_L),$$

where $D_{ps}$ is the polystyrene diameter, $D_2$ is the diameter of the particle to simulate, and $\rho_L$, $\rho_{ps}$, and $\rho_2$ are, respectively, the densities of, respectively, the liquid, polystyrene, and the particle to simulate, respectively. The expression is derived from fluid dynamic equations for laminar flow. The graph axes are Vz (vertical axis) versus particle size (horizontal axis) for polystyrene and silica glass spheres in water. If the objective is to set the rotational velocity of the stirring system to mix 13 μm glass spheres in water, which are not visible with the naked eye, the user adds 300 μm polystyrene spheres to water and increases the rotational velocity until a vortex is visible. Because 300 μm polystyrene particles require the same vertical velocity for lifting as 13 μm glass particles, it is a reasonable approximation that the rotational velocity to cause the onset of a vortex with 300 μm polystyrene particles will be the same rotational velocity required to cause the onset of a vortex with 13 μm glass spheres. Applicants assume that glass is representative of the worst-case high-density material of concern to pharmaceutical production.

Stirring Mechanism

Developing a circular motion is relatively simple. But a purely circular motion will result in a symmetric cyclonic streamline in the liquid, which will then suffer the same particle void in the bottle center as that developed using the magnetic stirring rods.

Figure 6:
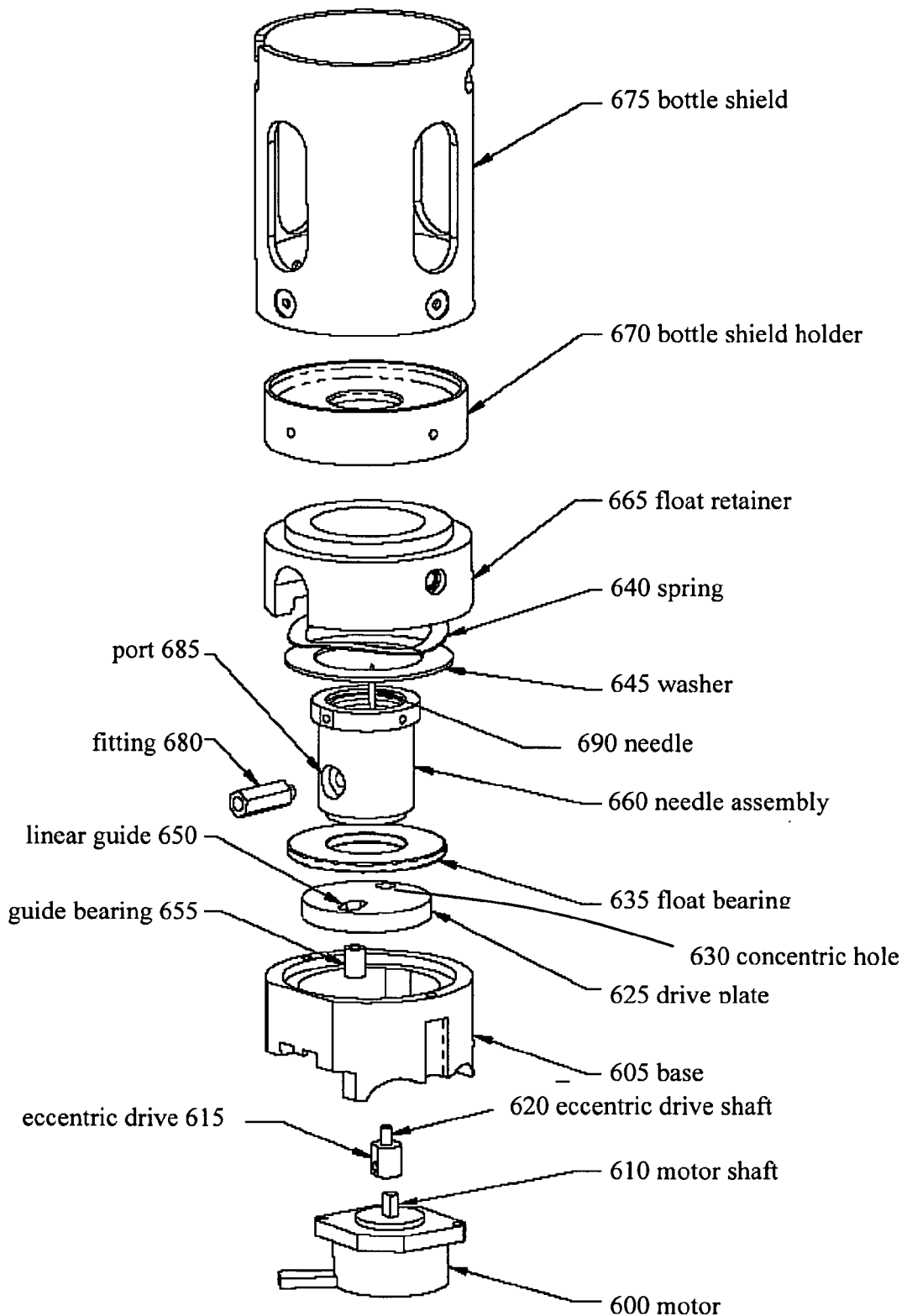
FIG. 6 is an exploded view of an embodiment of a stirring mechanism.
Figure 8:
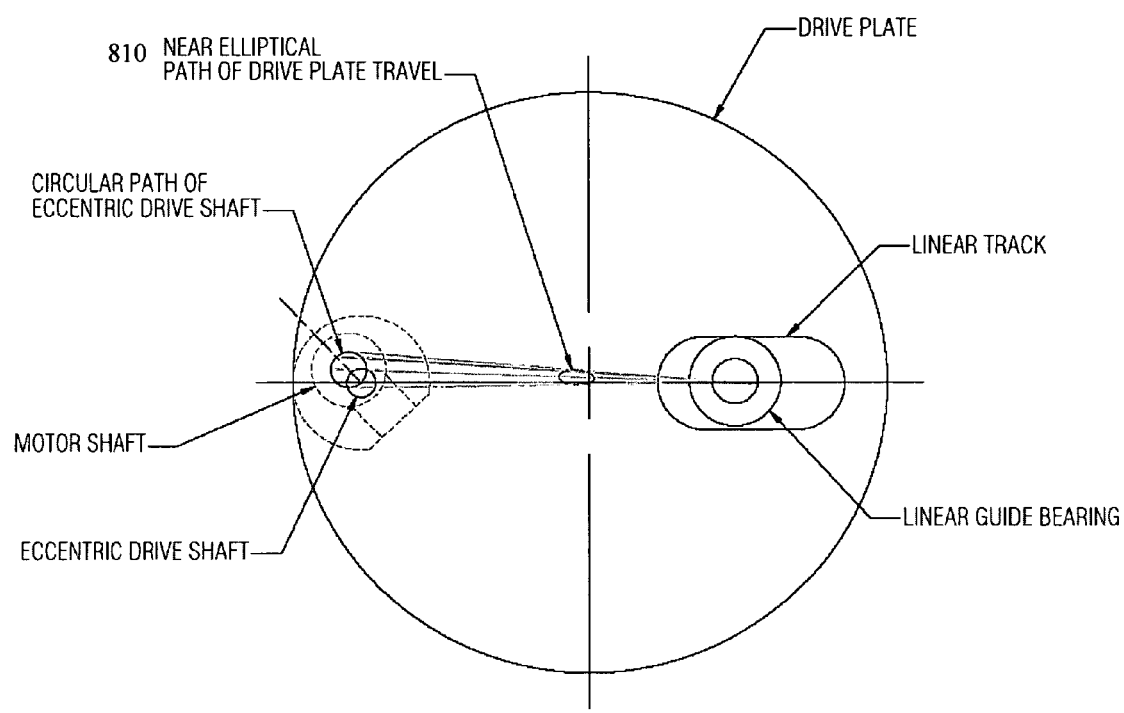
FIG. 8 depicts the motion path of the embodiment of the stirring mechanism of FIG. 6.

FIG. 8—described in more detail below under the heading "Details of the stirring mechanism and action"—depicts the motion path of the present embodiment of the stirring mechanism. This flow path has been empirically developed for the bottle shapes and sizes commonly used in pharmaceutical production. The path induces enough circular motion to induce a vortex capable of generation sufficient lift of particles, but contains enough linear motion to disturb the vortex without obliterating it. This linear motion induces a degree of chaos onto the cyclone that mixes the particles thoroughly. Although it induces a degree of chaos, the total motion is smooth enough to avoid inducing agitation or splashing in the liquid so as to avoid creating bubbles, micro bubbles, or cavitation. These can result in false positive readings in the sensor. One path that meets these conditions is nearly elliptical, and is shown in the center of FIG. 8. In the embodiments shown in the diagrams, this path is developed by using a stationary linear bearing engaging a linear track on the right side of the circular drive plate and an eccentric drive on the left side. A rotating motor shaft induces the eccentric motion with an offset drive pin connected to the drive plate. The sample bottle is connected to the drive plate as depicted in FIG. 6 and FIG. 7A, which will be described later.

Septum-Sealed Bottles and Delivery of Sample

Figure 15:
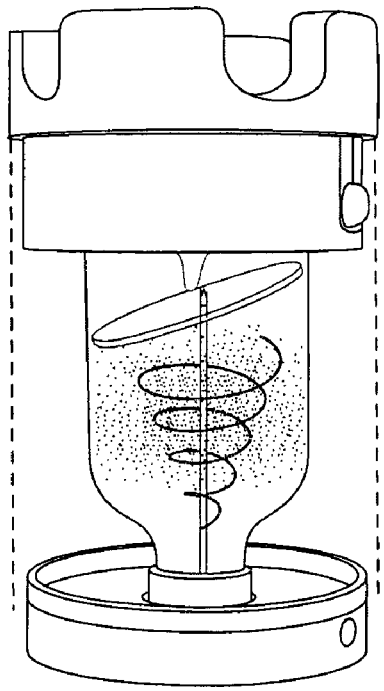
FIG. 15 is another frame, from the same video as FIG. 13, showing the uniform mixing of particles by the stirring mechanism of FIG. 6.

The mixing method may use a sealed container to prevent splashing and spilling during the vortex development. Smooth swirling of a liquid in a container creates a slanted liquid mass, as shown in, for instance FIG. 15. The slanted liquid mass may reach over the lip of an open bottle when the bottle is nearly full. To prevent this possibility, the sample bottle can be sealed on top.

Figure 10:
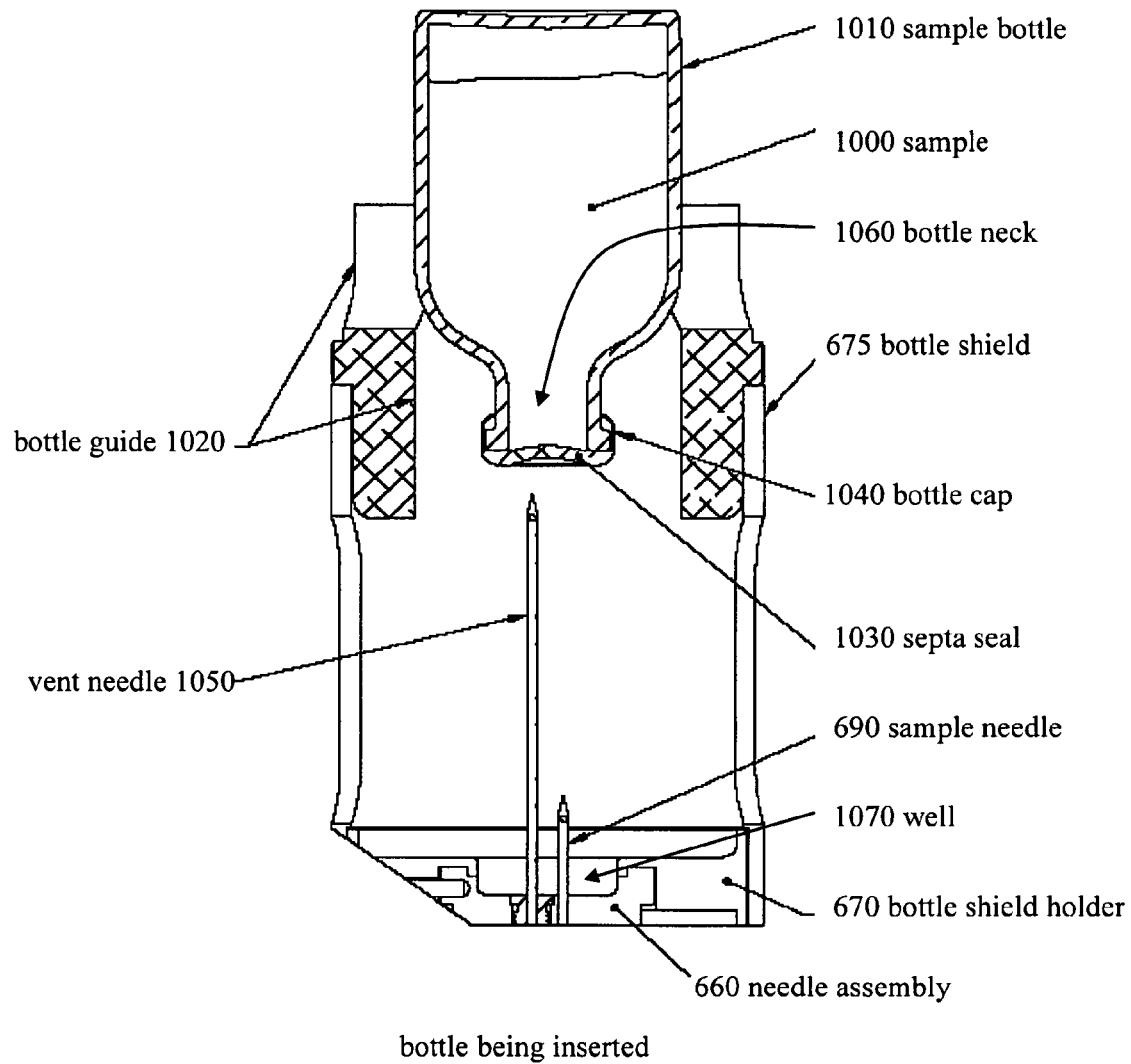
FIG. 10 is a cross-sectional diagram showing a sealed sample bottle being inserted into the stirring mechanism of FIG. 6.
Figure 11:
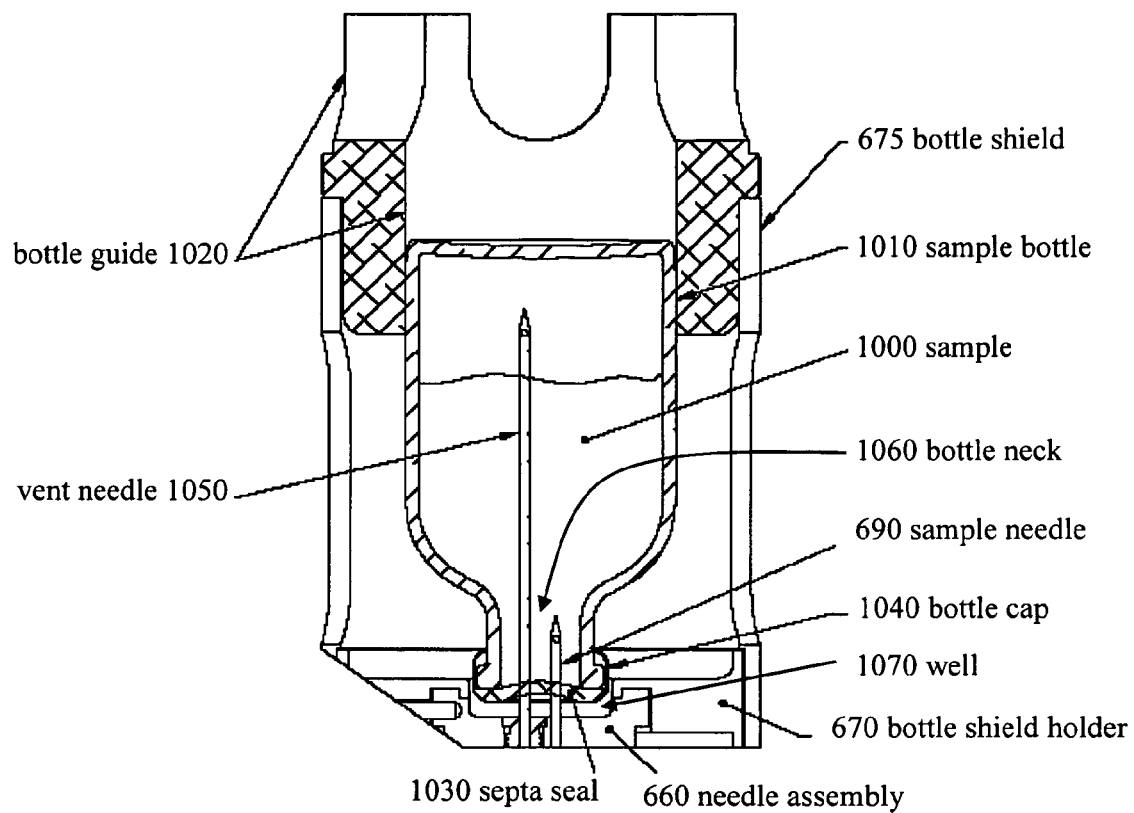
FIG. 11 is a cross-sectional diagram showing a sample bottle fully inserted into the stirring mechanism of FIG. 6.

FIG. 10 and FIG. 11—also described in more detail below—show the preferred embodiment of the sealing system. Inverting the bottle minimizes the tare volume. The tare volume is fluid from the previous sample trapped before the optical particle counter. This fluid (a) passes through the particle counter or other sensor without being counted as part of the current sample, and (b) is discarded. The narrower neck 1060 of the sample bottle 1010 in FIG. 10 and FIG. 11 allows nearly the entire sample to be drawn from the bottle. When a sample bottle 1010 is placed over sample needle 690 and vent needle 1050, the intake end of sample intake needle 690 resides in neck 1060 of the bottle. The system therefore can use all the liquid in the sample bottle except for a portion in the narrow neck below the intake end of sample needle 690. This helps extract the most sample liquid from the bottle, minimizing wastage. Minimizing the amount of tubing between the sample needle and the particle counting sensor or other testing device also reduces wastage.

The septum 1030 is an elastomeric seal encapsulated by a shield. The shield can be a metallic shield or made of other material, and may crimped or screwed onto the bottle. The seal protects the sample from airborne contamination and hermetically seals the sample. The use of a sealed mechanism also reduces particulate contamination.

Figure 9:
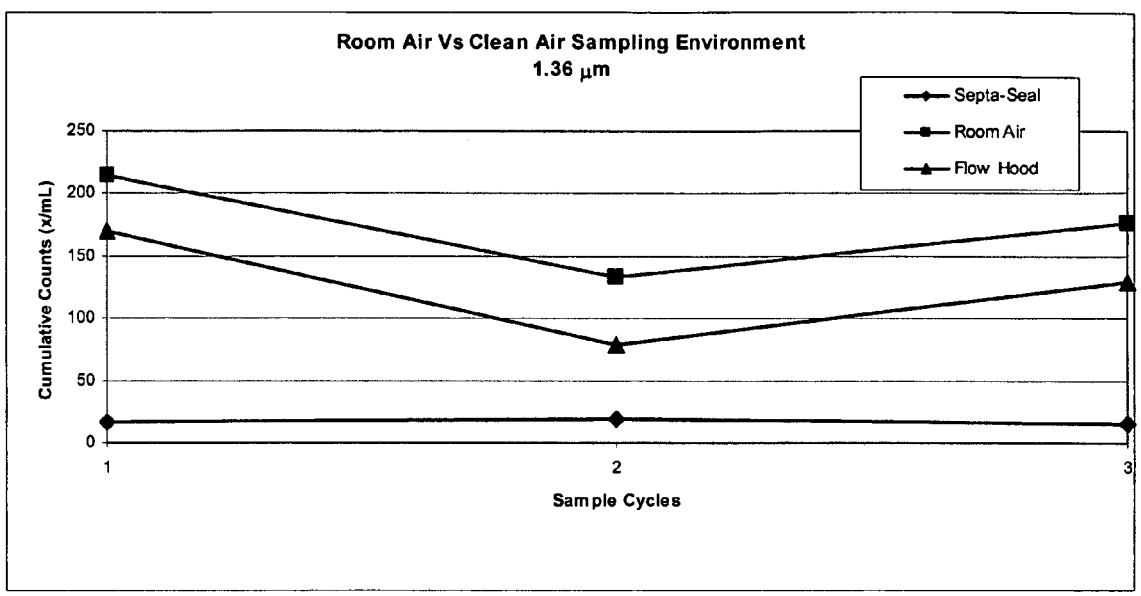
FIG. 9 is a graph of experimental data comparing particle counts in open, hooded, and sealed environments.

FIG. 9 is a graph of sample test data showing test-data particle of ultra-pure water counts in three different environments: room air in an open lab area, under a filtering flow hood with a HEPA filter, and a septa-seal. The room air and flow hood data show particle concentration in open bottles. This graph shows test data of the levels of contamination from testing an open sample bottle in an open lab area and under a filtering hood. Sealing the bottle reduces contamination of the sample.

Figure 12:
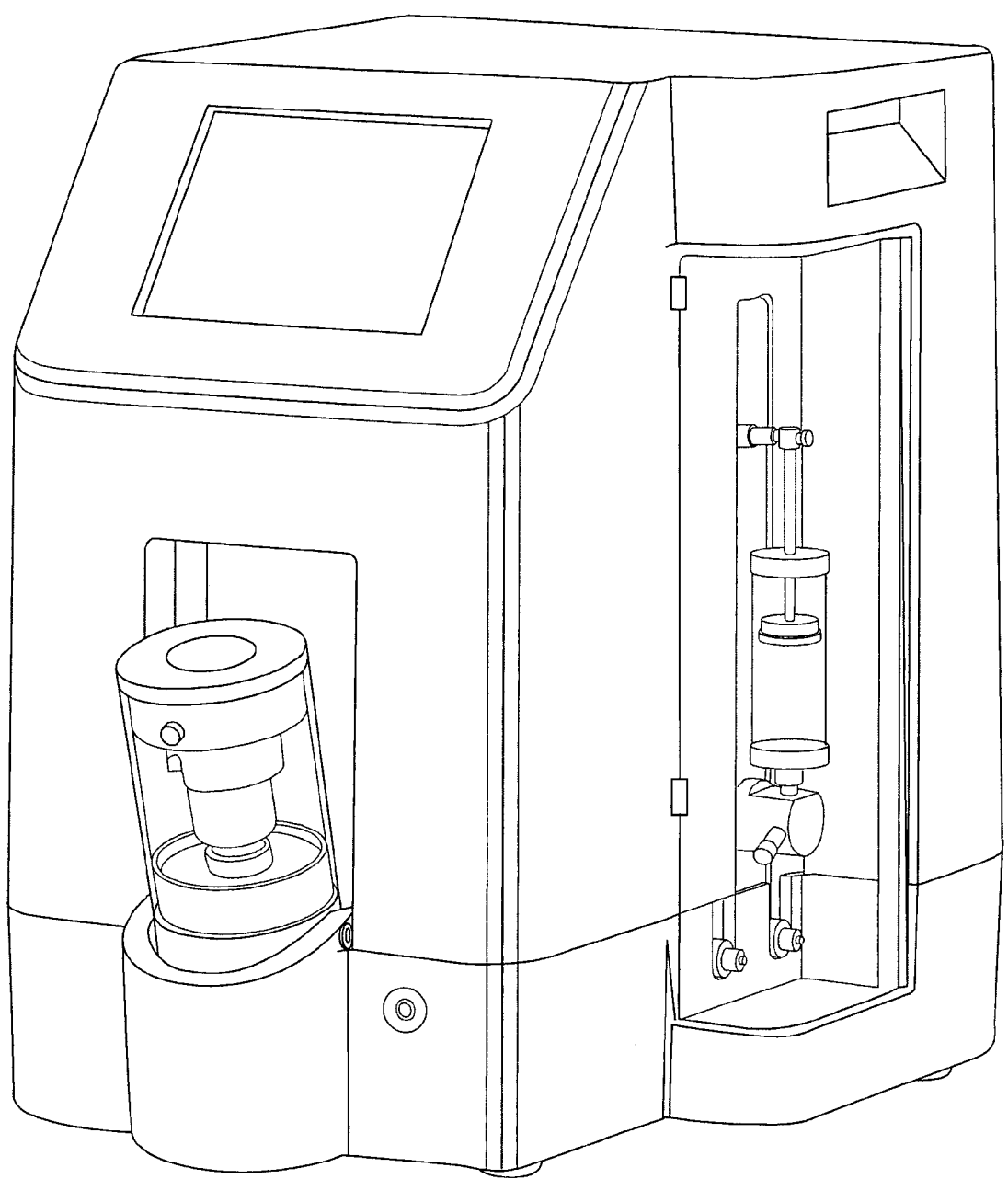
FIG. 12 is a pictorial view of a particle-counting instrument that includes an embodiment of a stirring mechanism.

FIG. 12 shows a particle-detecting instrument that contains an embodiment of the stirring mechanism described here, and that uses an embodiment of the sealing mechanism and delivery system described here. The stirring mechanism can be pivoted outward from the body of the instrument so that the user can easily insert a sample bottle.

The user pivots the sample mechanism outward, inverts the sample bottle, and inserts the sample bottle into the stirring mechanism over two hypodermic needles. As a user inserts the bottle onto the needles, an annular bottle guide 1020 guides the bottle into the correct radial position. Bottle guide 1020 is replaceable by different size guides, or can accommodate different size spacer rings within its internal diameter, so that the system can use sample bottles of different diameters.

As shown in FIG. 10 and FIG. 11, bottle 1010 is inverted in the particle counter and the septum 1030 is pieced by two hypodermic needles 690 and 1050 from below. The inversion also mixes the sample just prior to sampling. Two needles pierce the septum: sample needle 690 draws the sample from the bottom of the fluid (the normal top of the bottle) and the vent needle 1050 vents the vacuum at the top of the fluid (closer to the normal bottom of the bottle) due to the fluid evacuation. The venting may be to air or to another gas. The needles may also help secure the bottle from rotation as the circular motion of the stirring system imparts circular momentum on the bottle. Needles 690 and 1050 are shown as side-by-side, but may alternatively be concentric or otherwise arranged. The fluid may be withdrawn from the bottom by drawing through the sample needle or by introducing a gas under pressure though the vent needle or other passage into the bottle.

The vent needle is detachable and replaceable with vent needles of different lengths. This allows the system to use sample bottles of different heights.

In FIG. 12 the sample bottle has been completely inserted into the stirring mechanism in its outwardly pivoted position. The stirring mechanism then pivots inward so that the bottle is held vertically. The user then initiates mixing and testing. During testing, multiple aliquots, such as at least three aliquots, can be drawn from the sample bottle, and each is subject to testing for particulate matter. The testing, under control of software, uses a bright-field laser to count particles. For pharmaceutical purposes, the test results of the first aliquot may be discarded. The instrument may count particles within various size ranges and generate a report. The report may include the number of particles in each size range within each aliquot, the average number of particles within each size range, and the standard deviation of the aliquot.

The stirring mechanism mixes the sample before the aliquots are withdrawn from the sample bottle, and may also mix the sample while the aliquots are being withdrawn.

The instrument can be tested for particle counting accuracy, calibrated, or validated, by using a sample bottle containing a blank or a known concentration of particles of one or more sizes.

Details of the Stirring Mechanism and Action

FIG. 6, FIG. 7A, and FIG. 7B show the details of the present embodiment of the stirring mechanism. FIG. 6 is an exploded view, and FIG. 7A and FIG. 7B show section views. A stepper motor 600 drives the system. The stepper motor generates high torque at controlled velocities in a small package. Stepper motor 600 is rigidly connected to a base 605. A shaft 610 of stepper motor 600 is rigidly connected to the center of an eccentric drive 615. An eccentric drive output shaft 620 is rotationally coupled to a drive plate 625 through concentric hole 630 in drive plate 625. Drive plate 625 is free to move in the horizontal plane only and glides on a float bearing 635, which can be Rulon®. Rulon® is a specially compounded form of TFE fluorocarbon and other inert ingredients. Rulon® type J was selected for this embodiment as a maintenance-free bearing material with low coefficient of friction and excellent abrasion resistance. Float bearing 635 is restrained by a wave spring 640 and a shim washer 645.

Linear guide 650 is constrained to only linear motion and rotational motion about a guide bearing 655, which is rigidly connected to base 605. The eccentric input motion from drive 620, constrained by the linear and rotational motion of linear guide 650, causes substantially elliptical motion 810 at the center of drive plate 625, as shown in FIG. 8.

Drive plate 625 is connected to a needle assembly 660, which is free to rotate within the circumference of a float retainer 665. Needle assembly 660 is connected to a bottle shield holder 670 and a bottle shield 675. Bottle shield 675, as well as other parts that surround the bottle, may be made of transparent Plexiglas® or other transparent material so that the user can view the inside of the bottle while it is being stirred. A fitting 680 is hydraulically coupled to a port 685 of needle assembly 660 (shown in more detail in FIG. 10 and FIG. 11) and extracts sample 1000, via sample needle 690, through port 685, from sample bottle 1010. (For simplicity, FIG. 6 omits vent needle 1050 shown in FIG. 10 and FIG. 11.)

Sample bottle 1010 is concentrically inserted through bottle guide 1020, where septa seal 1030, which is part of a bottle cap 1040, is pierced by vent needle 1050 and then sample needle 690. When sample bottle 1010 is fully inserted onto needle assembly 660, the relatively narrow neck 1060 of bottle 1010 fits into a well 1070, which is configured to accept neck 1060. Also, when sample bottle 1010 is fully inserted onto needle assembly 660, the inlet of sample needle 690 lies within the relatively narrow neck 1060 of bottle 1010. Vent needle 1050 is vented to atmosphere to relieve vacuum build up in sample bottle 1010 during sample extraction. Bottle guide 1020, well 1070, and needles 690 and 1050 (both of which pierce the septum in the bottle), help constrain the bottle to the elliptical motion 810 (shown in FIG. 8).

The result is a gentle bottle motion that creates a helical vortex having upward velocity components capable of lifting particles from the bottom of the bottle, while the linear motion prevents the vortex from developing a cyclonic pattern that creates the particle voids associated with some prior-art methods. The resulting fluid motion is quasi-chaotic due to the complex geometry of the bottle and the superposition of linear and cyclonic motions. This explanation is supported by video images of the stirring mechanism with 300 μm polystyrene particles in water. The mechanical cam and drive mechanism disclosed above is capable of delivering the prescribed motion. The system is also simple in structure and easy to produce. Alternative mechanisms for creating a substantially elliptical motion are possible, including an X-Y table, a combination of a circular drive and a linear drive, and piezo-electric elements. Furthermore, these and other mechanisms can create a smooth helical vortex—one substantially lacking agitation or splashing in the liquid so as to avoid creating bubbles, micro bubbles, or cavitation—with upward velocity components capable of lifting particles and include a linear component that prevents the vortex from developing a pure cyclonic pattern that creates the particle voids associated with the present methods.

The system reduces contamination that may lead to false positives by not introducing an invasive stirrer, and by stirring and sampling from sealed bottles. As the bottle is inserted and withdrawn from the device, the motion between the septum and the needles cleans the exterior of the needles. The system reduces the need to perform mixing and/or sampling in a hood. The system results in uniform stirring and sampling from a portion of the bottle that correctly reflects concentration of particles or other matter in the bottle. Because the system is automatic, it also reduces or eliminates variability between individual users.

Figure 14:
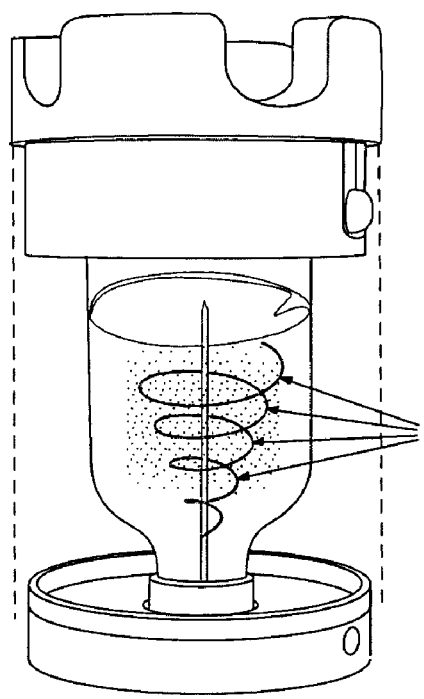
FIG. 14 is another frame, from the same video as FIG. 13, showing a vortex lifting particles off the bottom of the sample bottle.

The rotational speed needed to create a smooth vortex depends on a variety of factors having complex relationships, including bottle size, bottle shape, liquid viscosity and density, and whether the sample bottle has been mixed versus being completely settled. In the embodiment, the rotational speed therefore is adjustable, allowing the user to set the correct speed for a particular combination of bottle and sample liquid. The correct speed range can be determined empirically by testing a sample bottle of the desired shape and size, containing liquid of the desired viscosity and density, with the liquid also containing large polystyrene spheres, that will be visible to the eye as the bottle is stirred. The user places the sample bottle into the stirring mechanism, and gradually increases the rotational speed until a vortex appears that swirls the particles. FIG. 14 shows particles swirling in such a vortex in the stirring mechanism described here. (For clarity, the stirring mechanism has been removed from the particle counter, and the bottle shield has been removed from the stirring mechanism.) Continuing mixing at this speed results in the uniform mixing shown in FIG. 15

Figure 13:
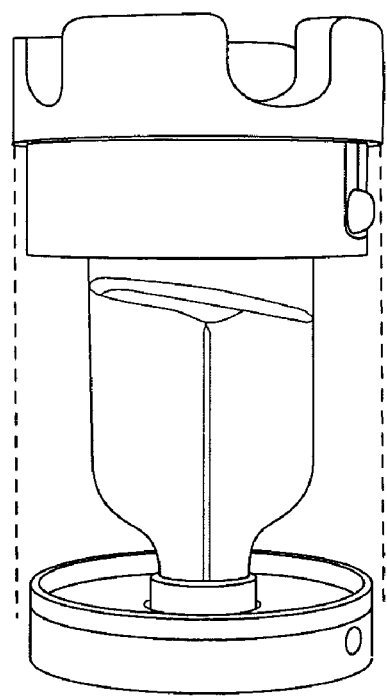
FIG. 13 is a frame of a video showing a developed wave front when a bottle is mixed using the stirring mechanism of FIG. 6.

It is desirable to use the minimal rotational speed required to induce the vortex for several reasons. If the speed is too high, the stirring will not be gentle, and the vortex will not be smooth—it will include bubbles or the like. The minimum speed uses less energy. It also tends to increase the working life of the system and its parts. The minimum speed also minimizes unnecessary disturbance of the liquid. It reduces the possibility of introducing bubbles or other undesirable side effects. As speed is increased, because of the elliptical shaped motion, the fluid begins to oscillate back and forth in the bottle, and the wave front climbs higher up the bottle wall with increasing speed. The wave front begins to change circumferential location on the glass and wet the bottle wall with increasing arc. The wave front begins to wet a substantial portion of the glass and eventually the drag of the water on the glass combined with the inertia of the water mass causes full rotation of the wave front around the bottle. FIG. 13 is a frame of a video showing a developed wave front.

Increasing rotational bottle speed increases the speed of the water rotation, which is now synchronized with the rotation of the bottle. The water eventually leaves a straight wetted line of water around the full circumference of the inner wall of the bottle. The wetted line tends to indicate optimum motion, but does not guarantee the particles will lift off the bottom of the bottle. This is done by visually witnessing the vortex development of FIG. 14 and thorough mixing of FIG. 15.

Further increases in rotational speed may begin to introduce turbulence and eventually cause destructive interference that causes the wave front to break the drag force on the glass. This will cause the wave front to collapse and stand stagnant despite the rapidly rotating bottle.

These motions are highly influenced by viscosity. Any surfactants in the fluid will change the motion patterns substantially. At least in relatively highly viscous fluids, such as 5606 hydraulic oil (with a viscosity of about 17 centipoises, while water is 1 centipoise), auto stirring may be incapable of stirring the mixture from rest. It is, however, capable of maintaining stirring the particles if the sample is mixed beforehand, such as by inverting the bottle over the needles.

Test Data

Figure 16:
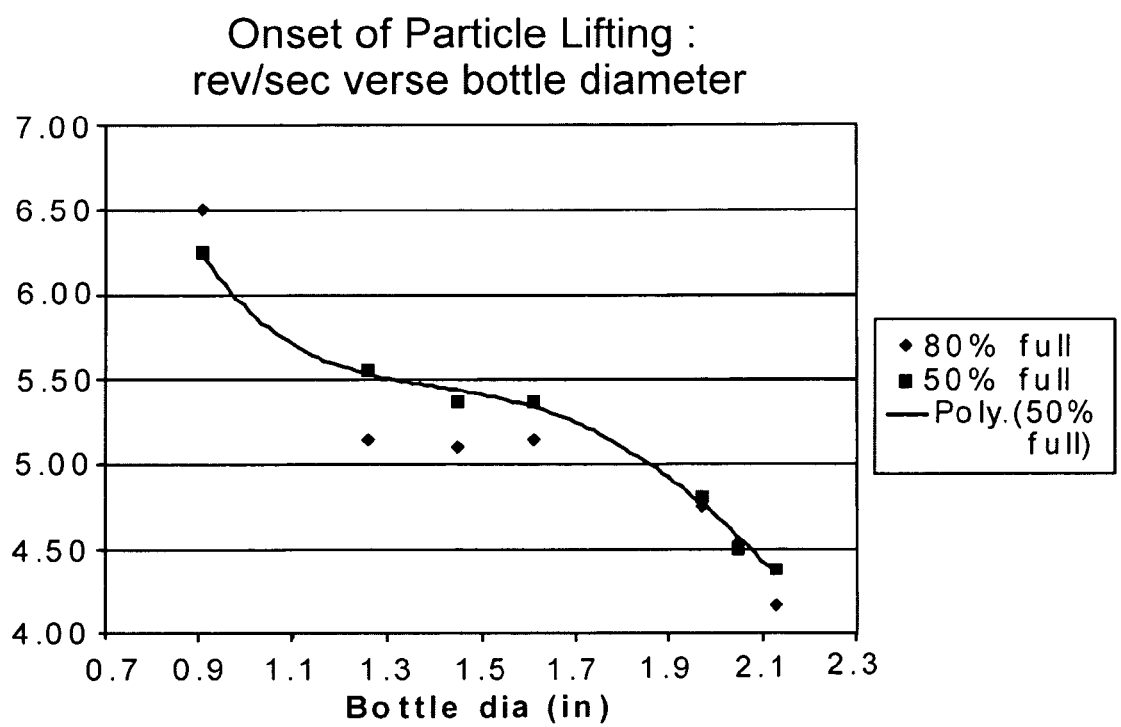
FIG. 16 is a graph showing the circular speed of the bottle to achieve the onset of particle lift for 300 μm polystyrene spheres.

FIG. 16 is a graph of the circular speed of the bottle to achieve the onset of particle lift for 300 μm polystyrene spheres. The complex curve like that shown in FIG. 16 is to be expected because the bottle geometry is complex. All the bottles have necks of the same size to accept the septa seal; this causes the vortex onset to vary in a nonlinear manner.

Bottles were mixed from the 90% full state and drained using the hypodermic needles. The complex vortex mixing was sustained until the bottles were empty.

It will be obvious to those having skill in the art that many changes may be made to the details of the above-described embodiments without departing from the underlying principles described here. For instance, non-invasive, sealed stirring can be used advantageously for testing of materials other than injectables and ophthalmic pharmaceuticals. It may also be used advantageously in conjunction with optical testing methods other than light extinction, such as light scattering, pseudo-bright-field, and colorimetric methods. It may also be used in conjunction with non-optical test methods.

The invention claimed is:

1. A stirring mechanism for noninvasive mixing of liquid and particulate matter held in a container, comprising:

a support configured to receive the container;

a drive mechanism operatively coupled to the support to impart to the container a non-circular path of motion that induces substantially uniform mixing of the liquid and the particulate matter held in the container;

the support including a coupling feature and the drive mechanism including a drive feature that cooperates with the coupling feature of the support to produce directional components of the non-circular path of motion, the directional components activating in the liquid a vortex that is capable of generating sufficient lift of the particulate matter and linear motion of an amount sufficient to introduce into the vortex a degree of chaos that thoroughly mixes the particulate matter in the liquid;

a particulate matter-detecting sensor; and a sample conduit that is capable of transmitting to the particulate matter-detecting sensor the liquid thoroughly mixed with particulate matter.

2. The stirring mechanism of claim 1, in which the non-circular path of motion is substantially elliptical.

3. The stirring mechanism of claim 1, in which:

the non-circular path of motion is in a substantially horizontal plane;

the support is configured to hold the container substantially perpendicular to the substantially horizontal plane; and the container is a sealed bottle.

4. The stirring mechanism of claim 3, in which the support includes a drive plate, and further comprising:

a drive plate first end comprising a linear cam;

a drive plate second end, substantially diametrically opposed to the drive plate first end, being driven by an eccentric drive;

a motor that drives the eccentric drive;

whereby the linear cam and eccentric drive cooperate to impart a substantially elliptical motion to the drive plate.

5. The stirring mechanism of claim 4 in which the linear cam constrains the drive plate second end to a substantially linear motion in the substantially horizontal plane.

6. The stirring mechanism of claim 1, in which the container includes a penetrable closure to form a sealed container, and further comprising a conduit configured to penetrate the penetrable closure and to withdraw the liquid from the container while the drive mechanism imparts to the container the non-circular path of motion.

7. The stirring mechanism of claim 6, in which:

the container has a narrow end; and the support is configured to hold the container so that the narrow end is positioned downward and so that the conduit withdraws the liquid from the narrow end.

8. The stirring mechanism of claim 1, in which the drive feature includes an eccentric drive having an eccentric drive shaft and driven by a motor, and in which the eccentric drive shaft and the coupling feature of the support cooperate to provide rotational coupling of the eccentric drive shaft to the support.

9. The stirring mechanism of claim 8, in which the motor has a stationary guide bearing, and in which the support includes a drive plate having a linear guide and the coupling feature is in the form of a hole, the linear guide and the hole positioned relative to each other on the drive plate to receive, respectively, the guide bearing and the eccentric drive shaft so that the eccentric drive imparts substantially elliptical motion to the drive plate.

10. The stirring mechanism of claim 9, in which the non-circular path of motion is oriented in a substantially horizontal plane and in which the linear guide receiving the guide bearing is constrained to substantially linear motion in the substantially horizontal plane.

11. The stirring mechanism of claim 1, in which the particulate matter-detecting sensor is of a light obscuration sensor type.

12. The stirring mechanism of claim 1, in which the particulate matter-detecting sensor is of a light scattering type.

13. The stirring mechanism of claim 1, in which the container is closed, and in which the sample conduit includes an end that is capable of penetrating the container.

14. The stirring mechanism of claim 13, in which the end is a needle.

15. The stirring mechanism of claim 1, in which the container has a narrow end, and in which the support is configured to receive the container such that the narrow end is oriented in a downward position to enable the sample conduit to withdraw from the narrow end the liquid thoroughly mixed with particulate matter.

16. The stirring mechanism of claim 1, in which the liquid held in the container has a top level, and further comprising:

a vent conduit that is capable of venting to air or other gas a vacuum produced at the top level by the transmitting to the particulate matter-detecting sensor the liquid thoroughly mixed with particulate matter.

17. The stirring mechanism of claim 16, in which the container is closed, each of the sample and vent conduits has an end that is capable of penetrating the container, and the end of the vent conduit is set above the top level.

18. The stirring mechanism of claim 17, in which each of the ends of the sample and vent conduits is a needle.

* * * * *